United States Patent [19]
Holmström

[11] Patent Number: 5,800,468
[45] Date of Patent: Sep. 1, 1998

[54] ACTIVITY-RESPONSIVE PACER WITH BIPOLAR SENSOR ELECTRODE

[75] Inventor: Nils Holmström, Järfälla, Sweden

[73] Assignee: Pacesetter AB, Solna, Sweden

[21] Appl. No.: 797,421

[22] Filed: Feb. 10, 1997

[30] Foreign Application Priority Data

Feb. 12, 1996 [SE] Sweden ............... 9600511

[51] Int. Cl.$^6$ .............................................. A61N 1/365
[52] U.S. Cl. .................................................. 607/17
[58] Field of Search ............................ 607/17, 19, 22, 607/26

[56] References Cited

U.S. PATENT DOCUMENTS

| | | |
|---|---|---|
| 4,779,618 | 10/1988 | Mund et al. |
| 4,827,933 | 5/1989 | Konig et al. ............... 607/22 |
| 4,870,967 | 10/1989 | Heinz et al. ............... 607/77 |
| 4,901,725 | 2/1990 | Nappolz et al. |
| 5,101,824 | 4/1992 | Lekholm ............... 607/22 |
| 5,228,437 | 7/1993 | Schroeppel |
| 5,480,441 | 1/1996 | Hudrik |

FOREIGN PATENT DOCUMENTS

0 620 420   10/1994   European Pat. Off.

Primary Examiner—William E. Kamm
Attorney, Agent, or Firm—Hill & Simpson

[57] ABSTRACT

A pacemaker system includes an electrode lead having a distal tip electrode for supplying stimulation pulses to cardiac tissue and a ring electrode, the electrode lead being connected to a cardiac stimulator. A detector is contained in a stimulator housing and is connected to the electrode lead for detecting electrical cardiac activity between said ring electrode and said tip electrode. Measurement of a signal dependent on physical activity of the subject in whom the pacemaker is implanted is obtained either by applying a voltage on the ring electrode during a predetermined measuring period and measuring a current through the ring electrode during at least a part of this period, or by, after detection of a QRS wave, applying a potential on the ring electrode and measuring the current between the housing and the ring electrode during the measuring period and also applying an alternating current between the tip electrode and the housing and measuring a voltage difference between the tip electrode and the ring electrode. The stimulation rate is then adjusted dependent on the measured value or values obtained.

21 Claims, 2 Drawing Sheets

FIG.1A
(PRIOR ART)
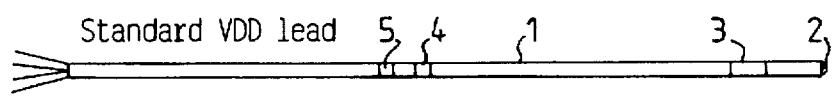
FIG.1B
FIG.1C
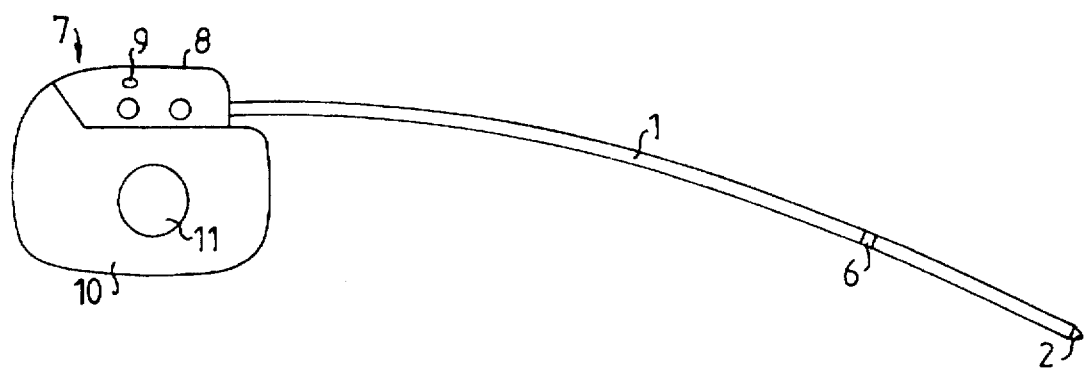
FIG.2
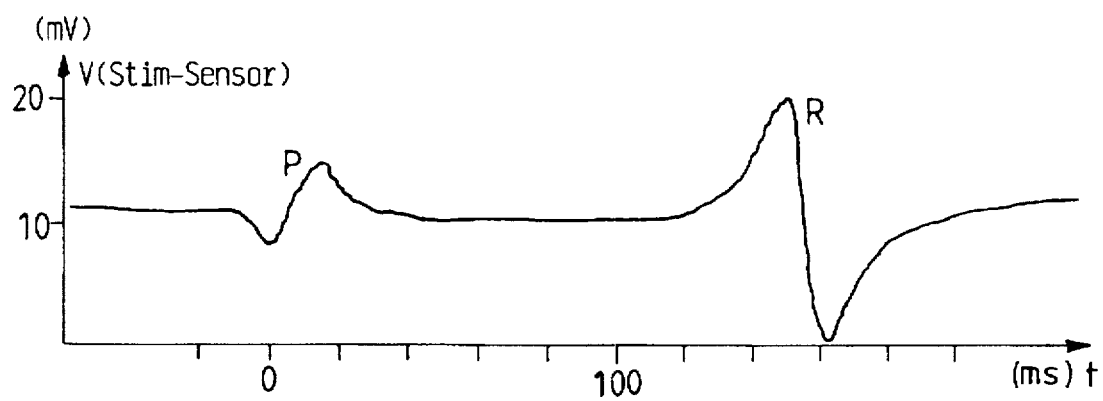
Measured voltage between stm electrode in apex and sensor in the atrium.
FIG.3

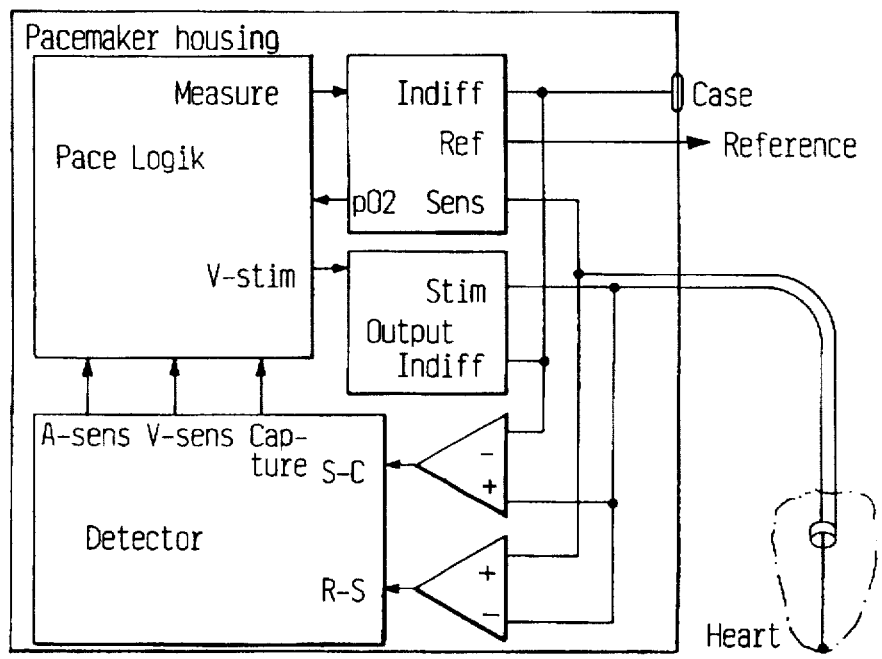
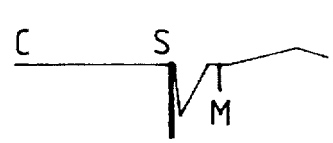
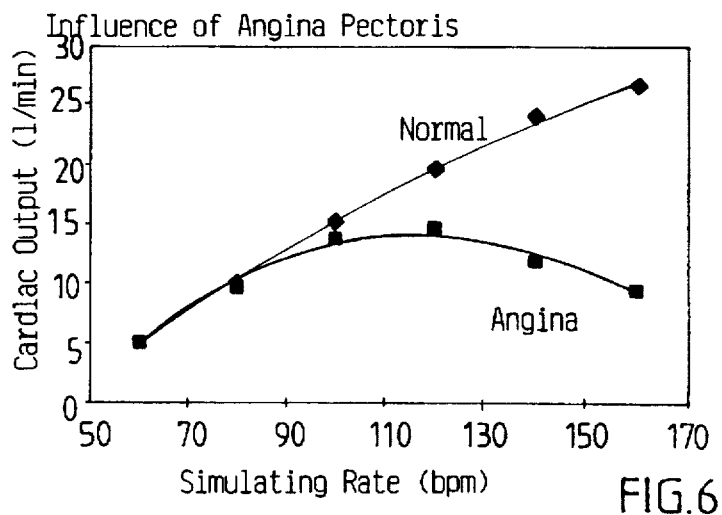

ACTIVITY-RESPONSIVE PACER WITH BIPOLAR SENSOR ELECTRODE

BACKGROUND OF THE INVENTION

1. Field of the Invention

The present invention relates to a means to achieve, in a pacemaker system, an automatic adjustment of the heart frequency to the patient's need. The invention also relates to a pacemaker system including such automatic adjustment.

2. Description of the Prior Art

A modern pacemaker system may have VDD electrodes carried by a single lead (cable) which measure the electrical activity in both the atrium and the ventricle and trigger the pacemaker to stimulate the ventricle in synchronization with the atrium. The VDD electrode arrangement is a four connector lead having a distal tip electrode and, spaced proximal to this, a ring electrode with a larger area than the tip electrode. These two electrodes are positioned in the right ventricle. The lead also carries two electrodes for placement in the atrium. The four electrodes can measure the electrical activity of the heart, the two electrodes in the atrium sensing the atrial activity and the two electrodes in the ventricle sensing the ventricular activity. If, as the result of the measured electrical activity, a pulse should be triggered, then this is done using the tip electrode as the stimulating electrode and using either the pacemaker housing as an indifferent electrode (the lead functioning as a unipolar electrode) or using the ring electrode as an indifferent electrode (the lead then functioning as a bipolar electrode).

Sensors may be implanted in the heart for measurement of patient activity-dependent parameters, e.g. oxygen pressure and blood flow. The pacing rate may be adjusted in accordance with the obtained sensor readings. A large number of leads and electrodes, however, are needed for this purpose.

U.S. Pat. No. 4,779,618 discloses a device for controlling the pacing rate control of a heart pacemaker in a manner which is intended to match the patient's current physiological requirements. This system has three or four electrodes in the body, i.e. the stimulation electrode, a counter electrode, a sensor electrode and possibly also a reference electrode. Both the stimulating electrode and the oxygen measuring electrode are loaded in parallel by the cathodic stimulating pulses. Thereafter the voltage between the stimulating electrode and the oxygen sensor or between the sensor electrode and the reference electrode is measured. From this measured potential the target pacing rate is calculated.

The problem of automatically adjusting the pacing rate in a pacemaker so as to track a patient's physiological requirements to using as few leads and electrodes as possible is at present addressed by using a physical activity sensor that is built-in the pacemaker capsule, e.g. a piezo-electrical crystal, which emits a so-called activity signal. No appliance on the lead is needed in this approach, only electrodes for p-wave detection and ventricular stimulation (stimulation electrode and possibly an indifferent electrode) are needed. This approach does not work for those types of sensors which it is desired to place in the blood flow or within the heart.

Therefore, in such cases an extra sensor lead or a single lead having three or more conductors is used and this may cause problems, e.g. disturbance of the blood flow or the hemodynamics.

SUMMARY OF THE INVENTION

An object of the present invention is to provide a method and apparatus by which a pacemaker system automatically, continuously adjusts its pacing rate, and thus the patient's heart beat rate, to the patient's current need.

It is a further object to provide such a method and apparatus which make the pacemaker system easy to implant and cause the least possible disturbance to the hemodynamics and physiology of the patient. Further it is an object to provide such a method and apparatus which allow the pacemaker system to employ as few leads as possible in the heart and also to use the necessary leads optimally to obtain the best possible functioning of the pacemaker.

These objects are achieved in a method where the same bipolar lead is used both as a detector of heart, for instance atrial, electrical activity (IECG) and as a physical activity sensor. Thereby it may be possible to obtain bipolar detection of both the atrial IECG and the ventricular IECG. It is possible to achieve unipolar stimulation of the ventricle and to detect one or more physiological activity parameters on the same bipolar lead.

The apparatus for performing this method includes a bipolar lead for a pacemaker system having a tip stimulation electrode and proximal thereto a ring electrode, functioning both as an electrode for p-wave detection and as an activity sensor measuring, e.g. blood oxygen pressure. The ring electrode may in the case of an oxygen pressure sensor be made of gold or smooth vitreous carbon.

According to one embodiment, the electrodes are arranged at such a distance from each other that when the tip electrode is introduced into the apex of the ventricle, the ring electrode will be positioned in the atrium or somewhere else where the atrial, activity can be detected and a measurement of a physiological activity parameter in mixed venous blood may be obtained (e.g. the opening to vena cava). The distance between the electrodes may be 6–15 cm, for instance 8–15 cm, preferably 10–12 cm.

According to another embodiment the electrodes are arranged at such a distance between each other that when the tip electrode is introduced into the apex of the ventricle, then the ring electrode will be also be positioned in the ventricle. In this case the distance between the electrodes may be 5–30 mm, preferably 10–20 mm.

Thus, the invention, is directed to a pacemaker system having an electrode lead carrying only a distal tip electrode for supplying stimulation pulses to heart tissue and, proximal thereto, a ring electrode, the electrode lead being attached to a heart stimulator. The heart stimulator includes a detector connected to the electrode lead for detecting electrical heart activity by a measurement between the tip electrode and the ring electrode. The ring electrode also serves as a sensor of at least one physical activity-dependent function and the heart stimulator includes means for applying a measuring voltage on said ring electrode during a specified measuring period and means for measuring a current through said ring electrode during at least part of this period. The heart stimulator also includes means for adjusting, dependent on said measured current, the stimulation pulse rate.

The invention is also directed to a system for controlling the pacing rate of a pacemaker in accordance with the patient's physical activity, the pacemaker being-adapted to be implanted in a human body and having a heart stimulator in a housing with a connector housing (header) including an integrated reference electrode. The system also includes a bipolar lead with a distal tip electrode, adapted to be implanted in a ventricle, and 6–15 cm proximal thereto a ring electrode. The system further includes means for detecting the potential difference between the tip electrode and the ring electrode, means for applying on the ring electrode, shortly after detection of a QRS wave, a physiological parameter measuring potential, relative to the reference electrode, for a short specified measuring time period, and means for measuring the current between the pacemaker housing and the ring electrode during at least a part of the measuring period, and means for triggering stimulating pulses between the indifferent pacemaker housing and the tip electrode at a rate dependent on the measured current.

The invention is also directed to a system for controlling the pacing rate of a pacemaker in accordance with a patient's physical activity, the pacemaker being adapted to be implanted in a human body and having a heart stimulator in a housing with a connector housing (header) including an integrated reference electrode, a bipolar lead with a distal tip electrode adapted to be implanted in a ventricle, and proximal thereto a ring electrode. The system includes means for detecting the potential difference between the tip electrode and the ring electrode, means for applying on said ring electrode, shortly after detection of a QRS wave, a physiological parameter measuring potential, relative to the reference electrode, for a short specified measuring time period, and means for measuring the current between the pacemaker housing and the ring electrode during at least a part of the measuring period. The system also has means for applying an alternating current between the tip electrode and the housing and means for measuring the voltage difference between the tip electrode and the ring electrode, and means for triggering stimulating pulses between the indifferent pacemaker housing and the tip electrode at a rate dependent on both the measured current and the measured voltage.

BRIEF DESCRIPTION OF THE DRAWINGS

FIG. 1A is a schematic illustration of a conventional VDD lead and FIGS. 1B and 1C, respectively, are schematic illustrations of first and second embodiments of a lead according to the invention.

FIG. 2 shows a pacemaker according to the invention.

FIG. 3 is a diagram showing the measured voltage in the pacemaker of FIG. 2, between the stimulation electrode in the apex and the sensor in the atrium during a normal heartbeat.

FIG. 4 is a block diagram of an inventive pacemaker system with a lead according to the invention.

FIGS. 5a–5c are three different voltage measurements obtained from the system in FIG. 4.

FIG. 6 is a diagram showing the change in cardiac output when the heart rate is increased, for a normal heart and for a heart exhibiting angina pectoris.

DESCRIPTION OF THE PREFERRED EMBODIMENTS

The lead in FIG. 1A is a standard VDD lead having four connectors and four electrodes, the tip electrode 2, the proximal ring electrode 3, (these two to be positioned in the ventricle), and the two atrial electrodes 4 and 5. Atrial activity is measured between the electrodes 4 and 5 and ventricular activity between the electrodes 2 and 3 or between the electrode 2 and the pacemaker housing. If an atrial depolarization is not followed by a ventricular depolarization, a stimulation pulse is delivered between the tip electrode 2 and the electrode 3 or the housing. No rate modulation depending on the physical activity of the patient is possible with this lead, except modulation in accordance with the sinus frequency.

The lead in FIG. 1B is an embodiment of a lead according to the invention. This lead stimulates in the ventricle, measures the heart electrical activity in both the ventricle and the atrium, in response to which it either inhibits or triggers a stimulation pulse, and is rate modulation programmable. This lead may be used in a pacemaker operating in the VDDR mode. The lead according to the invention is much less complex than the standard VDD lead shown in FIG. 1A. The lead in FIG. 1B has only two connectors and two electrodes, the tip electrode 2, to be positioned in the ventricle, and the ring electrode 6, replacing the electrodes 3, 4, 5 of the lead of FIG. 1A. The ring electrode 6 can be used to measure the atrial electrical activity as well as to sense a parameter dependent on the physical activity of the patient.

The lead in FIG. 1C is another embodiment of a lead according to the invention. The lead of FIG. 1C stimulates in the ventricle, measures the heart electrical activity in the ventricle, in response to which it can inhibit a stimulation pulse, and is rate modulation programmable (by a dual sensor). This lead has only two connectors and two electrodes, the tip electrode 2 and the ring electrode 6, both to be placed in the ventricle. They replace the electrodes 3, 4, 5 of the standard lead of FIG. 1A. The ring electrode 6 can be used to measure the ventricular electrical activity as well as to sense two parameters dependent on the physical activity of the patient. The lead of FIG. 1C may be used in a pacemaker system operating in the VVI-2R mode.

The pacemaker system in FIG. 2 includes a heart stimulator 7 having a housing IO and a bipolar electrode lead I attached thereto according to the embodiment of the invention shown in FIG. 1B. The housing 10 has a carbon surface layer 11, used as 15 the indifferent electrode, and an epoxy connector housing 8 with an integrated reference electrode 9. The lead 1 carries a ring sensor electrode 6 and a tip stimulation electrode 2. The stimulation electrode 2 is arranged at the distal end of the lead 1 to be inserted into the ventricle and is a conventional stimulation electrode made of, e.g., activated carbon. The sensor electrode 6 may be arranged about 11 cm from the tip electrode 2 and so as to be positioned in the atrium when the tip electrode 2 is inserted into the apex. The sensor electrode 6 may have an area in a range from about 1–10 $mm^2$ to about 10 $mm^2$, e.g. about 7 $mm^2$.

The sensor electrode 6 may, e.g., be an oxygen pressure sensor, an electrochemical blood flow sensor, an impedance sensor, a pH sensor, a carbon dioxide pressure sensor, etc.

The sensor electrode 6 may e.g. be made of gold, vitreous carbon, graphite, pyrolytic carbon, possibly containing small amounts of silicon, deposited on a metal such as titanium, platinum, iridium or iridium oxide.

During a detection phase the system monitors the voltage difference between the stimulation electrode 2 and the sensor electrode 6. The detected voltage is shown graphically, in the diagram of FIG. 3. By the morphology of the curve it is determined whether the detected event originates from the ventricle or the atrium. A p-wave has a derivative sign sequence (−+−) and a QRS wave has a first derivative sign sequence (+−+). Should the QRS wave fail to arrive after a p-wave, a stimulation pulse is delivered between the stimulation electrode 2 and the indifferent electrode on the pacemaker housing 10.

The sensor potential is floating all the time, except when the measurement pulse is delivered. The measurement pulse may be delivered during the absolute refractory time which occurs 2–100 ms, e. g. about 5 0 ms, after a QRS-wave or a stimulation pulse. Then the potential of the sensor 6 is forced to −0.8 V, relative to the reference electrode 9, for 15 ms. At this potential, oxygen in the blood will be reduced to hydroxyl ions at the sensor 6 and an electrical current will flow between the sensor 6 and the indifferent electrode 10. This current is dependent on the venous oxygen pressure. The pacemaker rate is determined from this sensor value. Also, the AV time can be optimized according to the oxygen pressure. Because the oxygen pressure is always measured directly after a stimulation pulse or a QRS-wave, the measurement pulse does not disturb the p-wave or the QRS detector. The measurement pulse may be delivered after each stimulation pulse or QRS-wave or at longer intervals, e.g. after every second, third, fourth or fifth stimulation pulse or QRS-wave, or at constant time intervals (triggered by the QRS-wave).

It is also possible with the sensor 6 to measure other parameters dependent on the physical activity. For instance, it is possible to measure the blood flow by using a flow sensor according to European Application 620 420.

FIG. 4 is a block diagram showing a pacemaker system with a combined VDD and sensor lead. The pacemaker housing includes pace logic, a detector, a stimulation pulse output unit and an oxygen pressure measuring unit. The lead 1 carries a tip stimulation electrode (S) and a ring sensor electrode (R). The pacemaker housing 11 ( C) serves as the indifferent electrode.

The pacemaker with a single bipolar lead shown in FIG. 4 is used for

1. Mixed venous oxygen pressure measurement in the atrium.
2. Bipolar atrial IECG sensing.
3. Bipolar and unipolar ventricular IECG sensing.
4. Ventricular capture sensing.
5. Ventricular unipolar stimulation with auto-threshold function.

The curves in FIGS. 5a, 5b, 5c are surface ECG curves and illustrate three different heart condition cases.

FIG. 5a: No QRS-wave is detected. The ventricular stimulation pulse is synchronized to the p-wave. The pacemaker operates in this manner in the presence of AV-block and a functioning sinus node.

FIG. 5b: Non-pathological beats. The pacemaker just monitors the heart function. If this situation is stable the activity sensor or sensors can be programmed "off."

FIG. 5c: No sinus wave is detected. During situations when the sinus rhythm cannot be used (e.g. during sinus arrest and atrial flutter) the pacemaker is operating in the VVIR mode until sinus is normal. The VVIR mode pacemaker modifies the pulse rate in accordance with the oxygen pressure measured at the ring sensor electrode.

FIG. 6 shows the development of the cardiac output with increasing heart rate in a normal heart and in a heart suffering from angina pectoris.

Patients with angina pectoris receive a decreased cardiac output when the heart stimulating rate is increased above a relatively low rate. The reason is that the myocardium becomes ischemic and the muscle stiff. The stroke volume is reduced rapidly with increased stimulating rate.

If only the oxygen pressure controls the heart rate of these patients, a positive feedback occurs and the rate increases simultaneously as the cardiac output decreases. This is a dangerous situation for the patient which can be avoided by using the second embodiment of the present invention (FIG. 1C). The stroke volume can be measured either by sensing the blood flow or by measuring the impedance. By monitoring the flow or the impedance profile during the physical heart beat, starting directly after measurement of partial oxygen pressure (pO2-measurement), morphology changes can be used to detect an ischemic heart. The stimulating rate then can be decreased to a basic rate and the heart will have an opportunity to relax.

Thus, using the lead of FIG. 1C a polarized pO2 measurement is made in the ventricle. Thereafter, the stroke volume is measured. An alternating current or voltage is applied between the tip electrode 2 and the indifferent electrode 11. The voltage between the ring electrode 6 and the stimulating electrode 2 is detected. The resulting measurement is processed to determine and monitor the impedance variations in the ventricle. During ischemia the impedance variations are smaller than normal.

The lead of FIG. 1C is also used for bipolar detection of ventricular activity in the conventional way.

Although modifications and might be proposed by those skilled in the art, it will be understood that my wish is to include within the claims of the patent warranted hereon all such changes and modifications as reasonably come within my contribution to the art.

I claim as my invention:

1. A pacemaker system comprising:
   an electrode lead having only a distal tip electrode for supplying stimulation pulses to heart tissue and, proximal to said distal tip electrode, a ring electrode;
   a cardiac stimulator, which emits stimulation pulses having a stimulation parameter associated therewith, to which said electrode lead is electrically connected;
   detector means for detecting electrical cardiac activity between said tip electrode and said ring electrode;
   means for applying a measuring parameter on said ring electrode during a predetermined measuring period and for measuring a measurement value through said ring electrode during at least a part of said period for sensing, via said ring electrode, at least one physical activity-dependent parameter;
   means for adjusting said stimulation parameter dependent on said measured value.

2. A pacemaker system as claimed in claim 1, wherein said measuring parameter is a potential and said measurement value is a current.

3. A pacemaker system as claimed in claim 1, wherein said measuring parameter is a current and said measurement value is a potential.

4. A pacemaker system as claimed in claim 1, wherein said stimulation pulse parameter comprises a stimulation rate of said stimulation pulses.

5. A pacemaker system as claimed in claim 1, wherein said stimulation pulse parameter comprises an A–V interval.

6. A pacemaker system as claimed in claim 1 wherein said ring electrode is disposed on said electrode lead at a distance from said tip electrode in a range between 6 and 15 cm.

7. A pacemaker system as claimed in claim 1 wherein said ring electrode is disposed on said electrode lead at a distance from said tip electrode in a range between 8 and 15 cm.

8. A pacemaker system as claimed in claim 1 wherein said ring electrode is disposed on said electrode lead at a distance from said tip electrode in a range between 10 and 12 cm.

9. A pacemaker system as claimed in claim 1 wherein said ring electrode is disposed on said electrode lead at a distance from said tip electrode in a range between 5 and 30 mm.

10. A pacemaker system as claimed in claim 1 wherein said ring electrode is disposed on said electrode lead at a distance from said tip electrode in a range between 10–20 and 30 mm.

11. A pacemaker system as claimed in claim 1 wherein said ring electrode comprises means for sensing at least one parameter selected from the group of parameters consisting of blood oxygen pressure, blood flow, impedance, pH value and carbon dioxide pressure.

12. A pacemaker system as claimed in claim 1 wherein said cardiac stimulator has a stimulator housing and a connector housing, said connector housing having a reference electrode on an exterior thereof.

13. A pacemaker system as claimed in claim 1 wherein said means for applying a measuring parameter comprises means for applying a plurality of measuring voltages on said ring electrode during a plurality of consecutive predetermined measuring periods, and means for measuring the current through said ring electrode during each of said measuring periods.

14. A pacemaker system as claimed in claim 1 wherein said cardiac stimulator has a housing having an indifferent electrode on an exterior thereof, and wherein said means for applying a measuring parameter comprises means for applying a DC measuring voltage on said ring electrode during a first measuring period and means for applying an AC current between said housing and said tip electrode during a second measuring period, said first and second measuring periods being consecutive, and means for measuring the current through said ring electrode during said first measuring period and means for measuring a voltage between said tip electrode and said ring electrode during said second measuring period.

15. A system for controlling a stimulation frequency of a cardiac pacemaker dependent on physical activity, said pacemaker adapted for implantation in a human body and having a cardiac stimulator in said housing which emits stimulation pulses at said rate, and a connector housing having a reference electrode on an exterior thereof, said system comprising:

a bipolar lead having a distal tip electrode adapted for implantation in a ventricle and a ring electrode disposed a distance from said tip electrode in a range from 6–15 cm;

means in said housing for detecting a potential difference between said tip electrode and said ring electrode;

means in said housing for applying, after detection of a QRS wave by said means for detecting, a physiological parameter measuring potential on said ring electrode, relative to said reference electrode, for a predetermined measuring time;

means in said housing for measuring a current between said housing and said ring electrode during at least a portion of said measuring time; and means for triggering said cardiac stimulator to emit pacing pulses between said pacemaker housing and said tip electrode at a rate dependent on said current.

16. A system as claimed in claim 15 wherein said pacemaker housing has an indifferent electrode formed by an external layer of carbon, and wherein said means for measuring the current between said housing and said ring electrode comprises means for measuring the current between the carbon layer and said ring electrode.

17. A system for controlling a stimulation frequency of a cardiac pacemaker dependent on physical activity, said pacemaker adapted for implantation in a human body and having a cardiac stimulator in said housing which emits stimulation pulses at said rate, and a connector housing having a reference electrode on an exterior thereof, said system comprising:

a bipolar lead having a distal tip electrode adapted for implantation in a ventricle, and a ring electrode proximal to said tip electrode;

means in said housing for detecting a potential difference between said tip electrode and said ring electrode;

means for applying, after detection of a QRS wave by said means for detecting, a physiological parameter measuring potential on said ring electrode, relative to said reference electrode, for a predetermined measuring time;

means for measuring a current between said housing and said ring electrode during at least a portion of said measuring time;

means for supplying an alternating current between said tip electrode and said housing;

means for measuring a voltage difference between said tip electrode and said ring electrode; and means for triggering emission of stimulation pulses by said cardiac stimulator between said housing and said tip electrode at a rate dependent on both the current measured between said housing and said ring electrode and the voltage difference measured between said tip electrode and said ring electrode.

18. A system as claimed in claim 17 wherein said pacemaker housing has an indifferent electrode formed by an external layer of carbon, and wherein said means for measuring a current comprises means for measuring a current between said carbon layer and said ring electrode.

19. A system as claimed in claim 17 wherein said ring electrode is disposed on said electrode lead at a distance from said tip electrode in a range between 5 and 30 mm.

20. A system as claimed in claim 17 wherein said ring electrode is disposed on said electrode lead at a distance from said tip electrode in a range between 6 and 15 cm.

21. A system as claimed in claim 17 wherein said ring electrode is disposed on said electrode lead at a distance from said tip electrode in a range between 8 and 15 cm.

* * * * *